United States Patent [19]

McCombie

[11] 4,237,051
[45] Dec. 2, 1980

[54] STEREOSPECIFIC PRODUCTION OF 6- OR 7-CARBON-SUBSTITUTED-β-LACTAMS

[75] Inventor: Stuart W. McCombie, West Orange, N.J.

[73] Assignee: Schering Corporation, Kenilworth, N.J.

[21] Appl. No.: 31,286

[22] Filed: Apr. 19, 1979

[51] Int. Cl.³ .................. C07D 499/00; C07D 501/02
[52] U.S. Cl. .......................... 260/245.2 R; 260/239.1; 544/16; 544/17; 544/18; 544/20; 544/24; 544/27; 544/30; 548/178
[58] Field of Search .......................... 260/239.1, 245.2; 544/18, 20, 27, 24, 16, 17, 30; 548/178

[56] References Cited

U.S. PATENT DOCUMENTS

| | | | |
|---|---|---|---|
| 3,198,804 | 8/1965 | Johnson et al. | 260/239.1 |
| 3,880,837 | 4/1975 | Lunn | 260/239.1 |
| 4,130,559 | 12/1978 | Tsinker et al. | 260/239.1 |
| 4,138,553 | 2/1979 | Ishimoto et al. | 260/239.1 |
| 4,143,046 | 3/1979 | Sheehan et al. | 260/239.1 |
| 4,147,699 | 4/1979 | Baldwin et al. | 260/239.1 |
| 4,150,157 | 4/1979 | Ferres | 260/239.1 |
| 4,154,845 | 5/1979 | Christensen et al. | 260/239.1 |
| 4,155,905 | 5/1979 | Dolfini et al. | 260/239.1 |

OTHER PUBLICATIONS

Hausler et al., *Helv. Chim. Acta,* 1327, (1967).
*J. Amer. Chem. Soc.,* 94, 1408, (1972).
Flynn, "Cephalosporins and Penicillins", Academic Press, pp. 193–199 and 670–673, (1972).
Ninomiya et al., *Chem. Pharm. Bull. Japan,* 22, 1398, (1974).
Sheehan, *J. Org. Chem.,* 39, 1444, (1974).
*J. Org. Chem.,* 41, 1578, (1976).
Sheehan, *J. Org. Chem.,* 42, 1012, (1977).

*Primary Examiner*—Natalie Trousof
*Assistant Examiner*—Vera C. Clarke
*Attorney, Agent, or Firm*—Barbara L. Renda

[57] ABSTRACT

Reaction of 6- or 7-diazo-β-lactams with allylic halides in the presence of a catalytic amount of metallic copper or a copper salt affords 6- or 7-carbon-substituted-β-lactams with the desired stereochemical configuration at the 6- or 7-position. Subsequent reduction with a trialkyl stannane affords useful intermediates for further syntheses affording 6- or 7-carbon-substituted-β-lactams.

11 Claims, No Drawings

STEREOSPECIFIC PRODUCTION OF 6- OR 7-CARBON-SUBSTITUTED-β-LACTAMS

The present invention relates to a process for the production of 6- or 7-carbon-substituted-β-lactams having the desired stereochemical configuration at the 6- or 7-position. More particularly, this invention provides a process for the preparation of a β-lactam of the formula

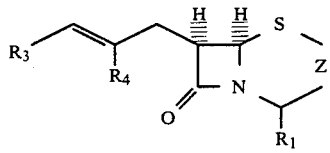
(I)

wherein $R_1$ is cyano or $COOR_2$ wherein $R_2$ is a readily removable ester-forming moiety, hydrogen or an alkali-metal cation;

$R_3$ and $R_4$ are independently hydrogen, lower alkyl, aryl or aralkyl;

Z is a group of the formula

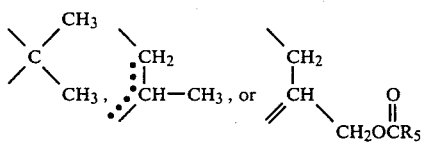

wherein $R_5$ is hydrogen, lower alkyl or aralkyl; and the dotted line indicates the optional presence of a double bond; which comprises (1) reacting a diazo-β-lactam of the formula

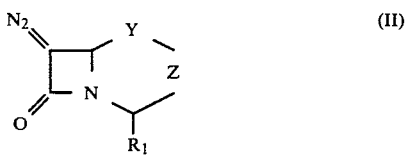
(II)

wherein Y is a sulfur or an oxygenated sulfur atom and Z, $R_1$, $R_3$, and $R_4$ are as hereinbefore defined; with an allyl halide of the formula

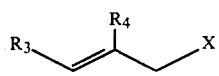
(III)

wherein $R_3$ and $R_4$ are as hereinbefore defined and

X is bromo or iodo;

in the presence of a catalytic amount of metallic copper or a copper salt; and where Y is an oxygenated sulfur atom, followed by transformation of the resultant oxygenated sulfur intermediate to a compound wherein Y is a sulfur atom; and (2) subjecting the resultant intermediate of the formula

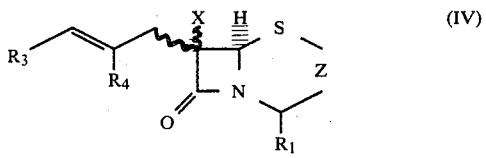
(IV)

wherein X, Z, $R_1$, $R_3$, and $R_4$ are as hereinabove defined, to reduction with a trialkyl stannane to afford the compound of formula I.

The lower alkyl groups referred to contain 1 to 6 carbon atoms and are exemplified by methyl, ethyl, propyl, butyl, pentyl, hexyl and the corresponding branched-chain isomers thereof.

The lower alkoxy groups referred to above likewise contain 1 to 6 carbon atoms and are exemplified by methoxy, ethoxy, propoxy, and the like.

The term "aryl" as used herein refers to phenyl substituted by one or more substituent groups selected from among chloro, bromo, fluoro, lower alkyl, hydroxy, nitro, amino, aminomethyl, lower monoalkylamino, lower dialkylamino, lower alkoxy and carboxy. Such aryl groups represented by $R_1$ can be, for example, 4-hydroxyphenyl, 3,4-dichlorophenyl, 2,6-dimethoxyphenyl, 4-methylphenyl, 2-fluorophenyl, 4-carboxyphenyl, 3-nitrophenyl, 4-aminophenyl, 3-aminophenyl, 4-dimethylaminophenyl, 4-aminomethylphenyl and 4-ethoxyphenyl.

The term "aralkyl" encompasses aryl-substituted lower alkyl groups such as benzyl, phenethyl, p-fluorobenzyl, o-tolylethyl and m-hydroxy-phenethyl.

The process of this invention initially involves the reaction of a diazo-β-lactam of formula II and the allyl halide of formula III in the presence of a catalytic amount of metallic copper or a copper salt to induce the decomposition of the diazo-β-lactam at temperatures of about 0°-50° C. to provide the intermediate of formula IV. The diazo-β-lactam utilizable in this step of the invention may be any type of readily removable ester-blocked acid, i.e., the compound of formula II wherein $R_1$ is $COOR_2$ or a nitrile, i.e., the compound of formula II wherein $R_1$ is cyano. Preferably, benzyl or benzhydryl esters are employed in the reaction wherein $R_1$ is $COOR_2$. The starting materials of formula II wherein Y is oxygenated sulfur are preferred due to the stability of the starting compound. However, the reaction using the equivalent sulfide also proceeds with good yields and avoids the need for a subsequent deoxygenation step.

The allyl halides of formula III utilizable in the present invention are those wherein the halogen is iodine or bromine with iodine being most particularly preferred. The allyl halide of formula III may be substituted by lower alkyl, aryl or aralkyl groups. Those compounds wherein $R_3$ and $R_4$ are methyl or phenyl are preferred.

The copper compound utilizable as a catalyst for this step of the instant invention may be almost any copper salt or finely divided elemental copper. Preferably, 1–10 mole percent of the copper or copper salt is utilized. The most preferred catalysts are cuprous chloride and copper (II)-2,4-pentanedioate.

In order to maximize the yield for this step of the instant invention, it is preferable to use a large excess of the allyl halide of formula III. Most preferably, allyl bromide or allyl iodide is used as the reaction medium. Substituted allyl halides of formula III are preferably diluted with a non-polar co-solvent such as methylene chloride. Polar solvents may also be used, e.g., dimethylformamide, dimethylsulfoxide or acetonitrile, but these provide poorer yields.

The reaction is preferably carried out at room temperature; however, depending on the nature of the starting materials, the reaction temperatures may range from about 0° to 50° C. Occasionally, warming to about 40° C. is utilized to initiate the reaction which is then continued without further heating.

The stereochemistry at C-6 or C-7 of the intermediate of formula IV is generally a mixture of alpha and beta compounds. Generally, use of the bromides gives a higher ratio of beta to alpha compounds, i.e., 5 to 6:1. Use of the iodides gives more approximately equal amounts of the alpha and beta isomers.

The reduction of step 2 to afford the cis product of formula I is accomplished using trialkyl stannane (trialkyl tin hydride). Preferably, tri-n-butyl stannane is utilized. The intermediate of formula IV is heated at about 60°–100° C. with 1–2 equivalents of the tin hydride in an inert solvent. Preferred solvents are tetrahydrofuran, benzene and toluene. Typically, the product is separated by chromatography in yields of greater than 80%.

The compounds of formula II wherein Y is an oxygenated sulfur atom may be obtained from the corresponding compounds wherein Y is sulfur by any of the conventional oxidation procedures, e.g., ozone, iodobenzene dichloride in aqueous pyridine, etc. An oxygenated sulfur penicillin compound, i.e., wherein Z is

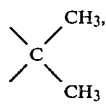

may then be converted to the corresponding cephalosporin, i.e., wherein Y is S and Z is

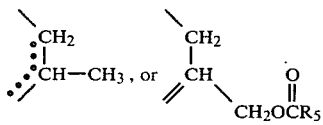

by various literature methods. See, for instance, Flynn, "Cephalosporins and Penicillins", Academic Press, pp. 193–199 and 670–673 (1972). By such methods benzyl 6β-allyl-6α-bromopenicillanate-1β-oxide may be converted to benzyl 7β-allyl-6α-bromo-3-methyl-3-cephem-4-carboxylate. The sulfoxide compound is also particularly useful wherein it is desired to convert a mixture of 2- and 3-cephem compounds to a pure 3-cephem compound.

The 6- or 7-diazo starting materials of formula II are preparable via a variety of literature methods or variations thereof. A preferred method involves degradation of the penicillin or cephalosporin side chain via the N-nitroso derivative as described by Hausler and Sigg, *Helv. Chim. Acta.*, 1327 (1967); and Sheehan, *J. Org. Chem.*, 39, 1444 (1974). This process involves treatment of the penicillin or cephalosporin, e.g., benzylpenicillin benzyl ester or benzhydryl ester, to form the N-nitroso derivative, followed by decomposition of the nitroso amide side chain with methylene chloride-pyridine or methylene chloride at about 40° C. to afford the diazo compound. An improvement of this process, omitting the pyridine and allowing the reaction to proceed at room temperature in a polar solvent, e.g., dimethylsulfoxide or dimethylformamide, affords a cleaner reaction and better conversion, i.e., >90%. This reaction sequence may be represented by the following scheme:

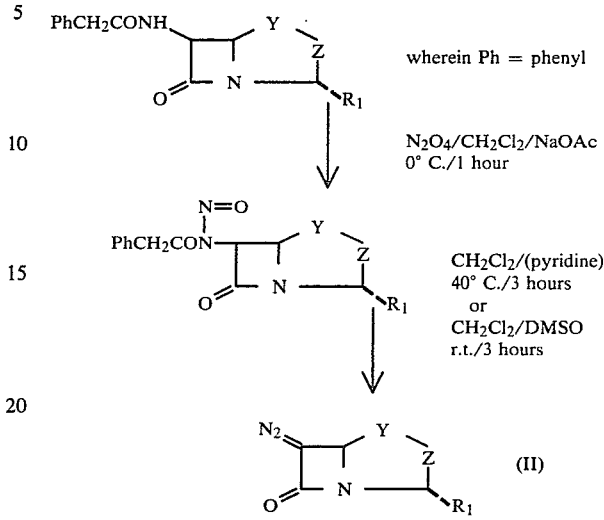

wherein Y, Z and $R_1$ are as hereinbefore defined.

Preferable by this route are the following:
benzyl 6-diazopenicillanate;
benzhydryl 6-diazopenicillanate;
6-diazopenicillanonitrile; and
benzyl 7-diazo-3-methylcephalosporanate.

Another modification of the decomposition step in the preparation of the starting materials of formula II is to utilize triphenylphosphine and water in place of the methylene chloride and pyridine according to the method of Sheehan, *J. Org. Chem.*, 42, 1012 (1977) to afford the hydrazone of the formula:

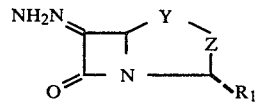

Oxidation of this hydrazone by the method of U.S. Pat. No. 3,880,837 affords the desired diazo compound. This route is particularly preferred for the cephalosporin starting materials of this invention. Preparable by this route are the following:
benzhydryl 7-diazo-3-methylcephalosporinate;
benzhydryl 7-diazo-3-acetoxymethylcephalosporinate; and
benzhydryl 6-diazopenicillanate.

An additional method for preparing the 6- or 7-diazo compounds of formula II involves diazotisation of the corresponding amino compounds using nitrous acid according to the procedure originally carried out by Hausler and Sigg, *Helv. Chim. Acta.*, 1327 (1967) and further delineated in *J. Amer. Chem. Soc.*, 94, 1408 (1972) and *J. Org. Chem.*, 41, 1578 (1976).

Once prepared, the compounds of formula I are utilizable to prepare various 6- or 7-substituted-β-lactams having useful antimicrobial activity, many of which are known in the art. For instance, ozonolysis of 6β-(allyl)-penicillanonitrile, benzyl 6β-(allyl)penicillanate or benzhydryl 6β-allylpenicillanate affords 6β-(formylmethyl)-penicillanonitrile, benzyl 6β-(formylmethyl)-penicillanate and benzhydryl 6β-(formylmethyl)penicillanate, respectively. This ozonolysis is carried out according to standard methodology.

The aldehyde obtained by the ozonolysis described in the preceding paragraph may then be subjected to reduction utilizing a mild reducing agent such as sodium borohydride to afford the corresponding alcohol. For instance, obtainable by this reaction is 6β-(2-hydroxyethyl)penicillanonitrile, benzyl 6β-(2-hydroxyethyl)penicillanate and benzhydryl 6β-(2-hydroxyethyl)penicillanate. The ester group of the preceding two compounds may, of course, be removed utilizing standard hydrogenolysis typically with a palladium catalyst to afford the resulting free acids. Workup with a weak base, e.g., potassium carbonate or sodium carbonate, will afford the potassium or sodium salts, e.g., potassium 6β-(2-hydroxyethyl)penicillanate or sodium 6β-(2-hydroxyethyl)penicillanate.

Oxidation of the aldehydes obtainable by the ozonolysis procedure affords the corresponding carboxylic acids. For instance, benzhydryl 6β-(formylmethyl)penicillanate treated with chromic acid in acetone and water affords benzhydryl 6β-(carboxymethyl)penicillanate.

Reaction of the foregoing carboxylic acids with suitable azides provides various homo-penicillanates. For instance, benzhydryl 6β-(carboxymethyl)penicillanate treated with diphenylphosphoryl azide and triethylamine at a reaction temperature of about 80° C. according to the method of Ninomiya, et. al., *Chem. Pharm. Bull. Japan*, 22, 1398 (1974), affords benzhydryl 6β-(carbonylaminomethyl)penicillanate which is typically not isolated. Treatment of this intermediate with the desired acid or alcohol provides homopenicillanates which then may be optionally deblocked. Obtainable in this method are potassium 6β-(phenylacetamidomethyl)penicillanate and potassium 6β-(ethoxycarbonylaminomethyl)penicillanate.

Treatment of benzhydryl 6β-(carbonylaminomethyl)penicillanate with trichloroethanol followed by a zinc/acetic acid reduction affords benzhydryl 6β-(aminomethyl)penicillanate. Conventional deblocking of this compound then affords 6β-(aminomethyl)penicillanic acid.

Several of the foregoing compounds are described by Sheehan, et. al. as having useful and interesting antimicrobial activity in German Pat. Nos. 2,416,492 and 2,643,085. However, 6β-(aminomethyl)penicillanic acid has not heretofore been described in any publication and is therefore a novel compound.

The 6β-(aminomethyl)penicillanic acid produced by the process of this invention possesses antibacterial activity. Additionally, it is a penicillinase inhibitor which may be used concomitantly with other penicillin-type antibiotics in infection therapy.

Thus, when tested in standardized microbiological assays, this compound exhibits activity vis-a-vis such organisms as Staphylococcus aureus, Klebsiella, Bacillus subtilis, and *Pseudomonas aeruginosa* at test levels of 0.1 to 100 μcg/ml. Thus, as antibacterial agents this compound is conventionally formulated for oral, intramuscular, intravenous or topical therapy.

Thus, the present invention includes within its scope pharmaceutical compositions comprising an antibacterially effective amount of the novel 6β-(aminomethyl)penicillanic acid with a compatible pharmaceutical carrier therefor, and a method of using such compositions for the treatment of microbial infections.

The dosage administered of this compound is dependent upon the age and weight of the animal species being treated, the mode of administration, and the type and severity of bacterial infection being prevented or reduced. Typically, the dosage administered per day will be in the range of 100–5000 mg with 500–1000 mg being preferred.

For oral administration, this compound may be formulated in the form of tablets, capsules, elixirs or the like. For parenteral administration it may be formulated into solutions or suspensions for intramuscular injection. Topical formulations include creams, ointments, gels and the like.

The following examples describe in detail compounds illustrative of the present invention and methods which have been devised for their preparation. It will be apparent to those skilled in the art that many modifications, both of materials and methods, may be practiced without departing from the purpose and intent of this disclosure.

PREPARATION A

Benzyl 6-Diazonpenicillanate

A solution of penicillin-G benzylester (25 g) in dichloromethane (150 ml) containing anhydrous sodium acetate (50 g) is stirred at 0°–5° C. and dinitrogen tetroxide (10 ml) added dropwise. After stirring for 45 minutes, ice (100 g) is added, followed by excess saturated aqueous sodium bicarbonate, in portions. After stirring for 15–20 minutes, the organic phase is separated, dried over anhydrous magnesium sulfate and filtered. The resulting solution is refluxed under nitrogen in an oil bath at 60° C. for 2½–3 hours. After cooling, the mixture is washed thoroughly with sodium bicarbonate solution, dried over anhydrous magnesium sulfate and evaporated to give the crude product as a thick yellow oil with infrared $\nu_{max}$ (film) at 2200 and 1740 cm$^{-1}$. This product is used immediately, or stored at −30° C. until required.

PREPARATION B

Benzhydryl 6-Diazopenicillanate

The title product is prepared according to the procedure of Example A from penicillin-G benzhydrylester and obtained as a yellow oil with infrared $\nu_{max}$ (film) at 2200 and 1745 cm$^{-1}$.

PREPARATION C

Benzyl 6-Diazopenicillanate-1β-Oxide

The title product is prepared in the same manner as detailed in Example A from penicillin-G sulfoxide benzylester, except that the nitrosation step requires 1.5 hours at 0°–5° C., and the dichloromethane reflux step requires only 1–1.5 hours for completion. The final washed and dried dichloromethane solution is evaporated to low volume, and crystallization completed by addition of excess ether. The title product is a yellow solid, melting point at about 134°–136° C. (decomp.) and infrared $\nu_{max}$ (nujol) at 2100, 1755 and 1735 cm$^{-1}$.

PREPARATION D

6-Diazopenicillanonitrile

Penicillin-G nitrile (24 g) is nitrosated as described in Example A, and the washed and dried solution of the N-nitroso compound evaporated to give a yellow solid. This is dissolved in dimethylsulfoxide (200 ml) and kept for 6 hours at 25° C. Then this solution is added to 2% aqueous sodium bicarbonate (500 ml) and extracted twice with 250 ml portions of dichloromethane. The combined extracts are washed with aqueous sodium chloride several times, dried over anhydrous magnesium sulfate and evaporated. The residue is crystallized from ether-hexane to give the title diazo compound as yellow prisms, melting point at about 90°–95° C. (decomp.) and infrared $\nu_{max}$ (nujol) at 2310, 2120 and 1760 cm$^{-1}$.

EXAMPLE 1

Benzyl 6β-Allyl-6α-Bromopenicillanate-1β-Oxide

A mixture of benzyl 6-diazopenicillanate 1β-oxide (0.70 g), allyl bromide (7 ml) and copper (II) 2,4-pentanedioate (0.1 g) is warmed to initiate reaction, which is then allowed to proceed with occasional warming, until nitrogen evolution is complete. The brownish mixture is applied to a silica gel column and eluted with 1:1 dichloromethane-hexane followed by dichloromethane. Fractions containing the product are pooled and evaporated to obtain the title product as a solid which crystallizes from dichloromethane-hexane as white plates, melting point at about 98°–100° C. and an $[\alpha]_D^{26}$ of +189.6° (CHCl$_3$, c=0.5).

EXAMPLE 2

Benzyl 6β-Methallyl-6α-Iodopenicillanate-1β-Oxide and Benzyl 6α-Methallyl-6β-Iodopenicillanate-1β-Oxide A mixture of benzyl 6-diazopenicillanate-1β-oxide (0.7 g) methallyl iodide (2 ml) and dichloromethane (2 ml) is warmed with copper (II) 2,4-pentanedioate (0.02 g) until the reaction is complete, and then the mixture is evaporated to dryness. The products are isolated by preparative thin layer chromatography on silica gel, eluting with a 2:1 v/v cyclohexane:ethyl acetate mixture.

The major, higher-$R_f$ product is determined to be benzyl 6β-methallyl-6β-iodopenicillanate-1β-oxide and is crystallized from ether to give white needles, melting point at about 119°–121° C. and an $[\alpha]_D^{26}$ of +151.8° (CHCl$_3$, c=0.5).

The lower-$R_f$ band provided benzyl 6α-methallyl-6β-iodopenicillanate-1β-oxide the minor product as a yellow oil with infrared $\nu_{max}$ (film) at 1780 and 1740 cm$^{-1}$.

EXAMPLE 3

Benzyl 6-Allyl-6-Bromopenicillanate

Benzyl 6-diazopenicillanate (from 50 gm of penicillin ester) is added as a solution in toluene (40 ml) to a stirred mixture of allyl bromide (200 ml) and cuprous chloride powder (3 g) with ice cooling. After addition (15 minutes), the mixture is stirred at room temperature for 0.5 hour, evaporated and chromatographed on silica gel (200 g). Elution is with carbon tetrachloride followed by 1% ethyl acetate in carbon tetrachloride. The appropriate fractions are evaporated to give the title product isomer mixture as a yellow oil (22.8 g) with infrared $\nu_{max}$ (film) at 1780, 1735 and 1630 cm$^{-1}$.

EXAMPLE 4

Benzyl 6β-Allyl-6α-Bromopenicillanate

A solution of 6β-allyl-6α-bromopenicillanate-1β-oxide (5 g) in dimethylformamide (40 ml) is stirred at 0°–5° C., and phosphorous tribromide (3.5 g) is added. Stirring is continued at room temperature for 1 hour. The mixture is then diluted with ether, washed with water, aqueous sodium bicarbonate and water and dried over anhydrous magnesium sulfate (MgSO4). Evaporation gives the title bromo compound as a pale yellow oil.

EXAMPLE 5

Benzhydryl 6-Allyl-6-Bromopenicillanate

Using benzhydryl 6-diazopenicillanate and the procedure of Example 3, there is obtained the title product as a pale yellow oil with infrared $\nu_{max}$ (film) at 1780, 1745 and 1640 cm$^{-1}$.

EXAMPLE 6

6-Allyl-6-Iodopenicillanonitrile

A mixture of 6-diazopenicillanonitrile (2 g), allyl iodide (15 ml) and copper (II) 2,4-pentanedioate (0.2 g) is warmed at 35°–40° C. for 15 minutes, then evaporated. The residue is chromatographed on silica gel with an eluant of 1:1 v/v hexane:dichloromethane. Evaporation of appropriate fractions gives the title product mixture as a pale yellow solid which rapidly darkens on exposure to light and has infrared $\nu_{max}$ (nujol) at 1770 cm$^{-1}$.

EXAMPLE 7

Benzyl 6β-Allylpenicillanate Benzhydryl 6β-Allylpenicillanate 6β-Allylpenicillanonitrile A solution of the particular 6-allyl-6-halogenopenicillanate (10 mmol), tri-n-butylstannane (15 mmol) and azobis-(isobutyronitrile) (0.5 mmol) in dry tetrahydrofuran (15 ml) is heated at reflux under argon until thin layer chromatography indicates complete reduction (0.5 hour for iodo compounds, 2–3 hours for bromo compounds). Ethyl acetate (50 ml) and sodium bicarbonate solution (25 ml) are added and the mixture is stirred for 0.5 hour. The organic phase is dried over anhydrous magnesium sulfate, evaporated and the residue chromatographed on silica gel (30 g), eluting with 10% dichloromethane-hexane until tin compounds are removed, then with dichloromethane to obtain the product. Obtained in high yield as colorless oils in this manner are:

Benzyl 6β-allylpenicillanate having an infrared $\nu_{max}$ (film) at 1770, 1730 and 1630 cm$^{-1}$; benzhydryl 6β-allylpenicillanate having an infrared $\nu_{max}$ (film) at 1770, 1735 and 1625 cm$^{-1}$ and 6β-allylpenicillanonitrile having infrared $\nu_{max}$ at 2300, 1775 and 1625 cm$^{-1}$.

EXAMPLE 8

Benzyl 6β-(Formylmethyl)penicillanate

A solution of benzyl 6β-allylpenicillanate (5 g) in methanol (30 ml) and dichloromethane (60 ml) is ozonized at −20° C. until thin layer chromatography indicates complete consumption of starting material. Dimethyl sulfide (3 ml) is added, and the mixture is kept at room temperature under nitrogen for 1 hour. The mixture is then washed with water and sodium chloride solution, dried over anhydrous magnesium sulfate and evaporated to give the title aldehyde as a thick oil with infrared $\nu_{max}$ (film) at 1780, 1735 and 1720 cm$^{-1}$.

EXAMPLE 9

Benzhydryl 6β-(Formylmethyl)penicillanate

The title product is prepared in the same manner as described in Example 8 from benzhydryl 6β-allyl-penicillanate and obtained as a thick oil with infrared $v_{max}$ (film) at 1780, 1745 and 1720 cm$^{-1}$.

EXAMPLE 10

6β-(Formylmethyl)penicillanonitrile

Following the procedure of Example 8, the title product is prepared from 6β-allylpenicillanonitrile as colorless prisms (from ether-hexane), melting point at about 115°–118° C. and with infrared $v_{max}$ (nujol) at 1780 and 1725 cm$^{-1}$.

EXAMPLE 11

Potassium 6β-(2-hydroxyethyl)penicillanate

A solution of benzhydryl-6β-(formylmethyl)penicillanate (0.82 g) in dichloromethane at 0°–5° C. is treated with an ice-cold solution of sodium borohydride (0.09 g) in ethanol (5 ml), and the mixture is immediately added to a stirred mixture of dichloromethane (20 ml) and 5% tartaric acid solution (20 ml). The organic phase is dried over anhydrous magnesium sulfate and evaporated to afford benzhydryl-6β-(2-hydroxyethyl)penicillanate. 0.6 g of this product in ethanol (25 ml), water (10 ml) and saturated aqueous sodium bicarbonate (3 ml) is hydrogenated at room temperature and 55 psi with shaking with 10% palladium-carbon (0.5 g) for 18 hours. The catalyst is filtered and the filtrate evaporated to 10 ml at 40° C. in vacuo. The residue is extracted with ether to remove diphenylmethane, and the aqueous phase is acidified with 5% phosphoric acid to pH 1.5–2 and extracted with 5×20 ml dichloromethane. The combined extracts are dried over anhydrous magnesium sulfate and evaporated to give the free acid as a foam. This foam is stirred in ether (50 ml) and a 0.6 M dichloromethane solution of potassium 2-ethylhexanoate (1.5 ml) added. The resultant title compound is filtered, washed with ether and dried in vacuo to give a fine white powder with infrared $v_{max}$ (nujol) at $\lambda_{max}$ 3250, 1770 and 1605 cm$^{-1}$.

EXAMPLE 12

6β-(2-hydroxyethyl)pencillanonitrile

6β-(formylmethyl)penicillanonitrile is reduced at 0° C. with sodium borohydride as in the method of Example 13. The title product is isolated by preparative thin layer chromatography in 1:1 ethylacetate:hexane as a colorless oil with infrared $v_{max}$ (film) at 3200, 2300 and 1775 cm$^{-1}$.

EXAMPLE 13

Potassium 6β-[2-(4-aminotetrahydro-1,4-thiazine-1,1-dioxide)ethyl]penicillanate

Benzyl-6β-(formylmethyl)penicillanate (0.35 g) and 4-amino tetrahydro-1,4-thiazine-1,1-dioxide (0.17 g) are stirred for 0.5 hour in chloroform (8 ml). The solution is then washed with 5% aqueous tartaric acid, dried and evaporated. The residue in ethanol (40 ml), water (10 ml) and sodium bicarbonate (0.12 g) is shaken for 3 hours in 60 psi of hydrogen with 10% palladium-on-carbon (0.6 g). The catalyst is removed by filtration and the filtrate diluted with water (10 ml) and evaporated in vacuo at 40° C. to 20 ml. The solution is then acidified to pH ~2 and extracted 5 times with 25 ml portions of chloroform, and the extracts dried and evaporated. The residue is dissolved in ether (10 ml) and treated with 0.6 M potassium-2-ethylhexanoate in dichloromethane (1.2 ml). The title product is collected by centrifuge, washed with ether and dried in high vacuum to give a hygroscopic solid with infrared $v_{max}$ (nujol) at 1770, 1670 and 1610 cm$^{-1}$.

EXAMPLE 14

6β-(Formylmethyl)penicillanonitrile-N,N-dimethylhydrazone

A mixture of 6β-(formylmethyl)penicillanonitrile (0.225 g), acetic acid (0.05 ml), dichloromethane (5 ml) and N,N-dimethylhydrazine (0.1 ml) is stirred for 15 minutes at 25° C. Washing with water and aqueous sodium bicarbonate, followed by drying and evaporation affords the title product as a thick oil with infrared $v_{max}$ (film) at 2300 and 1780 cm$^{-1}$.

EXAMPLE 15

6β-(2,2,-dimethoxyethyl)penicillanonitrile

A mixture of 6β-(formylmethyl)penicillanonitrile (0.25 g), dichloromethane (4 ml), trimethylorthoformate (3 ml) and p-toluenesulfonic acid (1 mg) is kept for 48 hours at room temperature. It is then diluted with chloroform and washed with sodium bicarbonate solution, dried to constant weight at high vacuum to remove trimethylorthoformate, giving the title compound as a pale yellow oil with an infrared $v_{max}$ (film) at 1775 cm$^{-1}$.

EXAMPLE 16

6β-(2-dimethylaminoethyl)penicillanonitrile

A solution of 6β-(formylmethyl)penicillanonitrile (0.225 g) in methanol (3 ml) and tetrahydrofuran (3 ml) is stirred with acetic acid (0.13 ml), dimethylamine hydrochloride (0.16 g) and sodium cyanoborohydride (0.13 g). After 0.5 hour, the mixture is shaken with ether and 10 ml 5% aqueous sodium carbonate and the ether phase is extracted with 2×10 ml of ice-cold 0.5 N hydrochloric acid. These extracts are brought to about pH ~9 with excess sodium carbonate and then extracted with ether. The extracts are dried (Na$_2$CO$_3$) and evaporated to give the title product as a waxy solid, melting point at about 60°–65° C. with an infrared $v_{max}$ (nujol) at 1780 cm$^{-1}$.

EXAMPLE 17

Benzhydryl 6β-(carboxymethyl)penicillanate

A solution of benzhydryl 6β-(formylmethyl)penicillanate (6.8 g) in acetone (200 ml) is stirred at 0°–5° C. and chromium (VI) oxide solution (11 ml of a solution containing 10 g CrO$_3$ and 8.5 ml H$_2$SO$_4$ in 90 ml water) is added. The mixture is then stirred for 1 hour at room temperature. After dilution with ether (400 ml) and 2% sodium bisulfite solution (300 ml), it is shaken thoroughly and the aqueous layer re-extracted with 100 ml ether. The combined organic solutions are washed with water and sodium chloride solution, dried and evaporated. The residue is crystallized from ether-hexane to give the title acid as white prisms melting point at about 138°–140° C., an $[\alpha]_D^{26}$ of +205.7° (CHCl$_3$, C=0.5) and infrared $v_{max}$ (nujol) at 3100, 1770 and 1740 cm$^{-1}$.

EXAMPLE 18

Benzhydryl 6β-(trichloroethoxycarbonylaminomethyl)penicillanate

A mixture of the acid prepared in Example 17 (0.425 g), triethylamine (0.16 ml) and diphenylphosphoryl azide (0.35 ml) is refluxed in 4 ml dry 1,2-dimethoxyethane for 15 minutes. Then, trichloroethanol (0.2 ml) is added, and refluxing continued for 1 hour. The mixture is worked up in ether-water, washed with sodium bicarbonate solution, dried and evaporated. The residue is chromatographed on silica gel with dichloromethane. Appropriate fractions are pooled and evaporated and the residue crystallized from ether-hexane to give the title compound, melting point at about 143°–145° C., with an $[\alpha]_D \approx$ of $+137.4°$.

EXAMPLE 19

Benzhydryl 6β-(ethoxycarbonylaminomethyl)penicillanate

The procedure of Example 18 is repeated with the trichloroethanol being replaced by ethanol (2 ml). Chromatography affords the title produce, which after crystallization from dichloromethane-hexane melts at about 110°–113° C. and has infrared $v_{max}$ (nujol) at 3250, 1780, 1735 and 1710 cm$^{-1}$.

EXAMPLE 20

Potassium 6β-(ethoxycarbonylaminomethyl)penicillanate

A solution of the ester prepared in Example 19 (0.5 g) and sodium bicarbonate (0.15 g) in water (12 ml) and ethanol (20 ml) is shaken in 60 psi hydrogen for 20 hours with 10% palladium-on-carbon (0.5 g). The catalyst is filtered, and the filtrate evaporated to 10 ml in vacuo at 40° C. and extracted with ether.

The ether is discarded and the aqueous solution acidified to about pH~2 and extracted with four 25 ml portions of dichloromethane. The extract is dried and evaporated, and the residue dissolved in ether (20 ml) treated with 0.6 M potassium 2-ethylhexanoate in dichloromethane (2 ml), and then diluted with hexane (20 ml). The salt is filtered, washed with ether and dried in vacuo at 25° C. to give the title product as a white powder with infrared $v_{max}$ (nujol) at 1765, 1710 and 1610 cm$^{-1}$.

EXAMPLE 21

Benzhydryl 6β-(phenylacetamidomethyl)penicillanate

Benzhydryl 6β-(carboxymethyl)penicillanate (0.85 g), triethylamine (0.32 ml) and diphenylphosphoryl azide (0.7 ml) are refluxed for 30 minutes in dry 1,2-dimethoxyethane ( 8 ml). Phenylacetic acid (0.6 g) is added, and refluxing continued for 24 hours. The mixture is then diluted with ether and washed with sodium bicarbonate solution, dried and evaporated. The residue is subjected to preparative thin layer chromatography using two developments in 3:1 hexane:ethyl acetate. The title product is eluted with ethyl acetate and obtained as a foam having infrared $v_{max}$ (nujol) at 3150, 1780, 1740 and 1675 cm$^{-1}$.

EXAMPLE 22

Potassium 6β-(phenylacetamidomethyl)penicillanate

A solution of the ester prepared in Example 21 (0.32 g) and saturated aqueous sodium bicarbonate (0.7 ml) in ethanol (20 ml) and water (7 ml) is shaken in 60 psi of hydrogen for 1.5 hours with 10% palladium-on-carbon (0.5 g). The mixture is filtered and evaporated to 15 ml in vacuo, and the solution is extracted with ether. The aqueous solution is acidified, extracted with dichloromethane and the extracts dried and evaporated. The crude acid is dissolved in ether and excess potassium 2-ethylhexanoate solution added. The precipitate is centrifuged, washed with ether and dried in vacuo to give the title product as a white powder having infrared $v_{max}$ (nujol) at 3250, 1765, 1675 and 1600 cm$^{-1}$.

EXAMPLE 23

6β-Aminomethylpenicillanic Acid

A solution of benzhydryl 6β-(trichloroethoxycarbonylaminomethyl)penicillanate (0.78 g) in 1,2-dimethoxyethane (10 ml) and acetic acid (1 ml) is stirred with zinc dust (1 g) and chloroform (0.2 ml) for 1.5 hour at room temperature. Ether (100 ml) and 10% sodium carbonate solution (25 ml) are added, the mixture shaken thoroughly and filtered, washing with ether. The organic phase is separated, dried over sodium carbonate and evaporated at room temperature in vacuo to a white foam.

This foam is dissolved in 70% ethanol (30 ml) and hydrogenated for 3.5 hours at 60 psi and 25° C. over a 10% palladium-on-carbon (0.35 g) catalyst. The catalyst is filtered and washed with water (20 ml) and the filtrate evaporated to about 30 ml in vacuo and extracted twice with 25 ml portions of ether. The aqueous phase is further evaporated at 30°–40° C. in vacuo to about 20 ml, and this solution lyophilized to give the title product as an off-white powder with infrared $v_{max}$ (nujol) at 3300, 1765 and 1610 cm$^{-1}$.

What is claimed is:

1. A process for the preparation of a β-lactam of the formula:

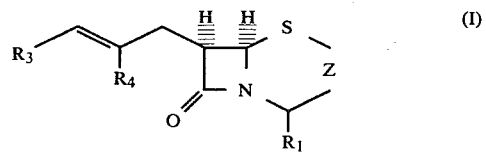

wherein

R$^1$ is cyano or COOR$_2$ wherein R$^2$ is a readily removable ester-forming moiety, hydrogen or an alkali-metal cation;

R$^3$ and R$^4$ are independently hydrogen, lower alkyl, aryl or aralkyl;

Z is a group of the formula

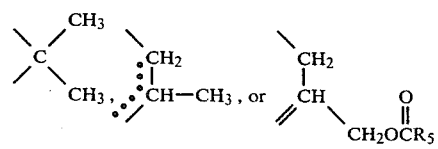

wherein R$_5$ is hydrogen, lower alkyl or aralkyl; and the dotted line indicates the optional presence of a double bond; which comprises (1) reacting a diazo-β-lactam of the formula

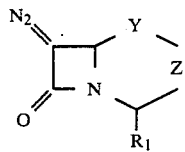 (II)

wherein Y is a sulfur or oxygenated sulfur atom, and Z, $R_1$, $R_3$, and $R_4$ are as hereinbefore defined; with an allyl halide of the formula

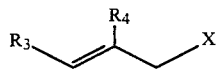 (III)

wherein $R_3$ and $R_4$ are as hereinbefore defined and X is bromo or iodo;

in the presence of a catalytic amount of metallic copper or a copper salt; and where Y is an oxygenated sulfur atom, followed by transformation of the resultant oxygenated sulfur intermediate to a compound wherein Y is a sulfur atom; and (2) subjecting the resultant intermediate of the formula

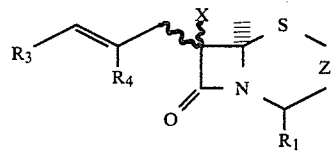 (IV)

wherein X, Z, $R_1$, $R_3$, and $R_4$ are as hereinabove defined, to reduction with a trialkyl stannane to afford the compound of formula I.

2. The process according to claim 1 wherein Z is a group of the formula

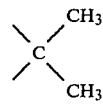

3. The process according to claim 2 wherein $R_3$ and $R_4$ are both hydrogen.

4. A process according to claim 2 wherein Y is sulfur.

5. A process according to claim 2 wherein Y is oxygenated sulfur.

6. A process according to claim 1 wherein 1–10 mole percent of the copper or copper salt is utilized.

7. A process according to claim 6 wherein the copper salt is cuprous chloride.

8. A process according to claim 6 wherein the copper salt is copper(II)-2,4-pentanedioate.

9. A process according to claim 1 wherein the temperature of Step (1) is room temperature.

10. A process according to claim 1 wherein the trialkyl tin hydride used in Step (2) is tri-n-butyl stannane.

11. The compound which is 6β-(aminomethyl)-penicillanic acid.

* * * * *